(12) United States Patent
Zerfas

(10) Patent No.: US 7,234,677 B2
(45) Date of Patent: Jun. 26, 2007

(54) PINCH CLAMP

(75) Inventor: Gerald Bernard Zerfas, Kentwood, MI (US)

(73) Assignee: Z-Man Corporation, Kentwood, MI (US)

( * ) Notice: Subject to any disclaimer, the term of this patent is extended or adjusted under 35 U.S.C. 154(b) by 0 days.

(21) Appl. No.: 11/253,208

(22) Filed: Oct. 18, 2005

(65) Prior Publication Data

US 2006/0081797 A1    Apr. 20, 2006

Related U.S. Application Data

(60) Provisional application No. 60/619,701, filed on Oct. 18, 2004.

(51) Int. Cl.
*F16K 7/04*    (2006.01)
(52) U.S. Cl. ........................................ 251/10
(58) Field of Classification Search ............... 251/10, 251/9, 4
See application file for complete search history.

(56) References Cited

U.S. PATENT DOCUMENTS

| | | | | |
|---|---|---|---|---|
| 682,172 | A | * | 9/1901 | Chaddock ............... 251/10 |
| 1,347,931 | A | * | 7/1920 | Bowes, Jr. .............. 251/10 |
| 2,127,257 | A | * | 8/1938 | Hornberger ............. 251/10 |
| 2,643,848 | A | | 6/1953 | Hoffman |
| 2,682,874 | A | * | 7/1954 | Hickey ................. 251/10 |
| 3,176,691 | A | | 4/1965 | Ericson |
| 3,204,636 | A | | 9/1965 | Kariher et al. |
| 3,612,475 | A | * | 10/1971 | Dinger ................. 251/10 |
| 3,698,043 | A | | 10/1972 | Batts |
| 3,698,681 | A | | 10/1972 | Lacey |
| 3,713,622 | A | | 1/1973 | Dinger |
| 3,766,925 | A | | 10/1973 | Rubricius |
| 3,779,507 | A | | 12/1973 | Clarke |
| 3,822,052 | A | | 7/1974 | Lange |
| 3,824,654 | A | | 7/1974 | Takabayashi |
| 3,847,370 | A | | 11/1974 | Engelsher |
| 3,874,042 | A | | 4/1975 | Eddleman et al. |
| 3,942,228 | A | | 3/1976 | Buckman et al. |
| 4,053,135 | A | | 10/1977 | Saliaris |
| 4,097,020 | A | | 6/1978 | Sussman |
| 4,235,412 | A | | 11/1980 | Rath et al. |
| 4,266,751 | A | | 5/1981 | Akhavi |
| 4,346,869 | A | | 8/1982 | MacNeill |
| 4,429,852 | A | | 2/1984 | Tersteegen et al. |
| 4,434,963 | A | | 3/1984 | Russell |
| 4,453,295 | A | | 6/1984 | Laszczower |
| D283,918 | S | | 5/1986 | Jacobson |
| 4,589,626 | A | | 5/1986 | Kurtz et al. |
| 4,643,389 | A | | 2/1987 | Elson et al. |
| 4,673,161 | A | | 6/1987 | Flynn et al. |
| D318,123 | S | * | 7/1991 | Yokoyama et al. ........ D24/129 |
| 5,035,399 | A | | 7/1991 | Rantanen-Lee |
| 5,083,741 | A | | 1/1992 | Sancoff |

(Continued)

*Primary Examiner*—John Bastianelli
(74) *Attorney, Agent, or Firm*—Price, Heneveld, Cooper, DeWitt & Litton, LLP

(57) ABSTRACT

The present invention provides a pinch clamp that includes a support leg member and a coupling leg member, which are interconnected by a curved portion, and a generally upwardly extending anchor portion having at least one anchoring flange located at the distal end of the anchor portion. The pinch clamp also contains at least one tabular member which extends outward from the anchor portion, which facilitates opening of the pinch clamp.

18 Claims, 3 Drawing Sheets

U.S. PATENT DOCUMENTS

| | | |
|---|---|---|
| 5,174,477 A | 12/1992 | Schafer |
| 5,203,056 A | 4/1993 | Funk et al. |
| 5,238,218 A | 8/1993 | Mackal |
| 5,951,519 A | 9/1999 | Utterberg |
| 6,113,062 A * | 9/2000 | Schnell et al. ................ 251/10 |
| 6,161,812 A | 12/2000 | Guala et al. |
| 6,196,519 B1 | 3/2001 | Utterberg |
| 6,234,448 B1 | 5/2001 | Porat |
| 6,644,618 B1 * | 11/2003 | Balbo ......................... 251/10 |

* cited by examiner

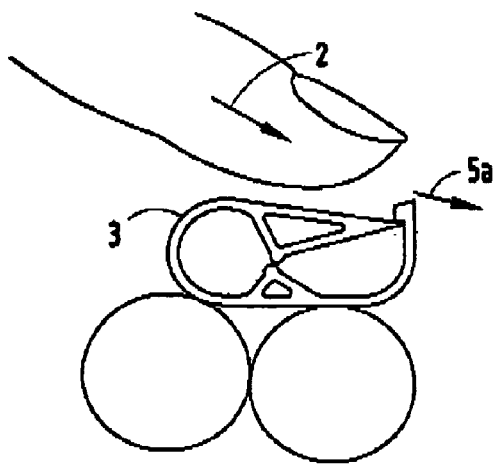
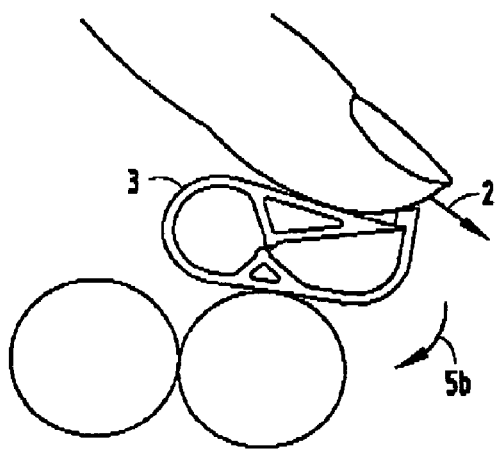
FIG. 1A
PRIOR ART
FIG. 1B
PRIOR ART
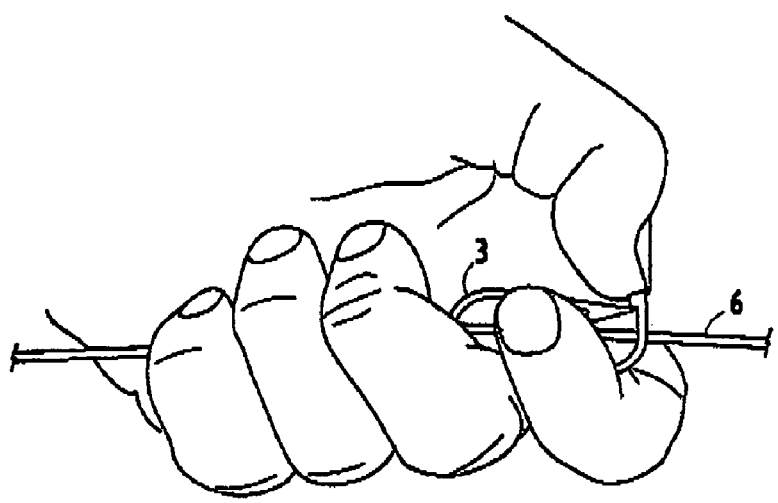
FIG. 1C
PRIOR ART
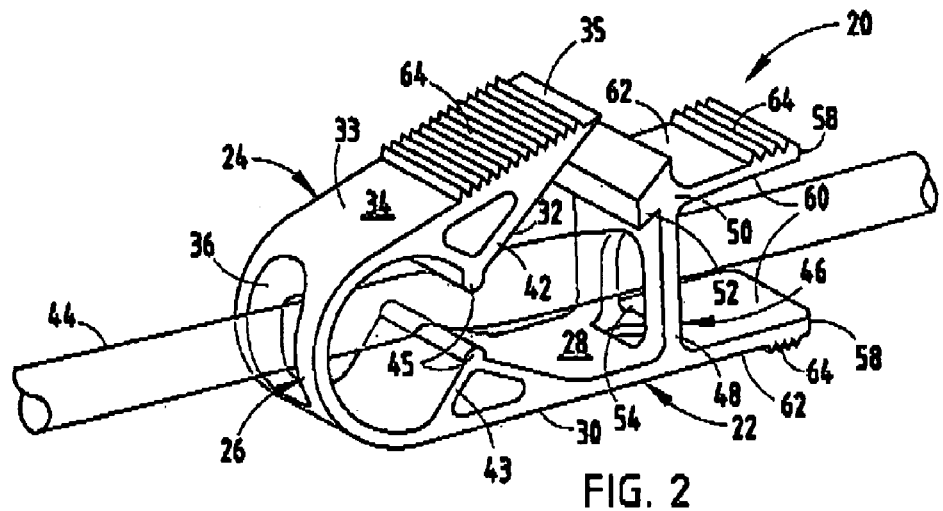
FIG. 2

PINCH CLAMP

CROSS-REFERENCE TO RELATED APPLICATIONS

This application claims the benefit under 35 U.S.C. § 119(e) of U.S. Provisional Application Ser. No. 60/619,701, filed Oct. 18, 2004, which is hereby incorporated by reference in its entirety.

BACKGROUND OF THE INVENTION

Pinch clamps are well known in the art and have been used for many years to control the flow of fluids through tubing. Despite the widespread use of pinch clamps, the current devices and methods for opening the pinch clamps are awkward, and sometimes even hazardous, especially when used on patients in the medical field. When a patient undergoes a medical procedure, it is extremely advantageous for the staff to be able to quickly and safely change the flow of fluids without disturbing the orientation of the tubing. Currently available pinch clamps are awkward and difficult to open one-handed. As seen in FIG. 1C, in order for a person to open such pinch clamps one-handed, a person must grip the pinch clamp 3 with at least one finger while simultaneously applying a force to the pinch clamp clasp with the thumb. As shown in FIGS. 1A and 1B, one cannot open this particular known pinch clamp with one hand without firmly gripping the clamp with one's finger(s) while trying to open the clamp with one's thumb or other finger(s). One attempting to open this particular known pinch clamp 3 with one hand without firmly gripping the clamp with one's finger(s) while trying to open the clamp with one's thumb or other finger(s) applies a force 2 which causes the pinch clamp to move/slide forward across one's fingers (as shown in FIG. 1A by arrow 5a), or rotate in a circular direction around one's finger (as shown in FIG. 1B by arrow 5b). When a pinch clamp is used on a tubing line in a medical application, it is extremely advantageous for the staff to be able to quickly and safely open and close a pinch clamp that is installed on the tubing. Since the tubing is typically attached to a patient, any pushing or pulling on the tubing may be painful or life-threatening to the patient. Because currently available pinch clamps require that the pinch clamp and associated tubing 6 (See FIG. 1C) be firmly grasped, undesirable pushing or pulling on the tubing line may occur. And because currently available pinch clamps require an awkward and difficult hand and thumb action to open the pinch clamp with one hand, undesirable pushing or pulling on the tubing line 6 may occur. The degree of difficulty to open the present pinch clamp with one hand is directly impacted by the size and strength of one's hand. Present pinch clamps are also more difficult to release when medical staff wear gloves, which are typically worn for the protection of the staff and the patient. Pinch clamps may be used during highly stressful medical procedures where every second counts. As such, fumbling with awkward equipment should be kept to a minimum. Therefore, there is an unfulfilled need for a pinch clamp which is easily manufactureable, easy to use, and that quickly and safely releases without substantially altering the orientation of the tubing.

SUMMARY OF THE INVENTION

The present invention generally relates to an improved, more ergonomic pinch clamp. An embodiment of the present invention includes a pinch clamp having a support leg member, a coupling leg member capable of repeatedly moving between an open position and at least one closed position, a curved portion interconnecting the support leg member and the coupling leg member, and an anchor portion having an anchoring flange for retaining the coupling leg member in a closed position, the improvement of a pair of release tabs that are configured to receive finger(s) wherein the release tabs cooperate to bend the anchoring portion and release the coupling leg member from the anchoring flange when force is applied to the release tabs.

Another embodiment of the present invention generally relates to a pinch clamp that includes a support leg member having a coupling leg member facing surface and an outer surface; a coupling leg member having a support leg member facing surface and an external surface where the coupling leg member is moveable between an open position and at least one closed position and vice versa. The coupling leg member or the support leg member further includes a pinch portion. The pinch clamp further includes a curved portion interconnecting the support leg member and the coupling leg member; an upwardly extending anchor portion having at least one anchoring flange facing the curved portion and capable of retaining the coupling leg member when the coupling leg member is in a closed position; and at least one tabular member engaged with the anchor portion and extending outwardly away from the curved portion.

BRIEF DESCRIPTION OF THE DRAWINGS

FIG. 1A is a side elevational view of a prior art pinch clamp in the closed position and grasped between a thumb and two other fingers (shown as circles);

FIG. 1B is a side elevational view of a prior art pinch clamp in the closed position and grasped between a thumb and two other fingers (shown as circles);

FIG. 1C is a perspective view of a prior art pinch clamp being grasped to allow the clamp to be opened using the thumb to apply force to the flange of the clamp;

FIG. 2 is a perspective view of an embodiment of a pinch clamp of the present invention in the open position;

DETAILED DESCRIPTION OF PREFERRED EMBODIMENTS

For purposes of the description herein, it is to be understood that the specific devices and processes illustrated in the attached drawings and described in the following specification are simply exemplary embodiments of the inventive concepts defined in the appended claims. Hence, specific physical characteristics relating to the embodiments disclosed herein are not to be considered as limiting, unless the claims expressly state otherwise.

Figure 3:
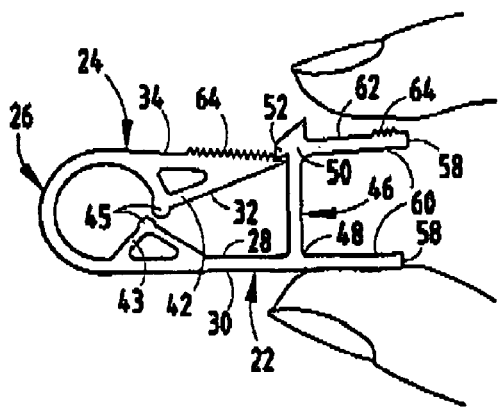
FIG. 3 is a side view of an embodiment of a pinch clamp of the present invention in the closed position.
Figure 7:
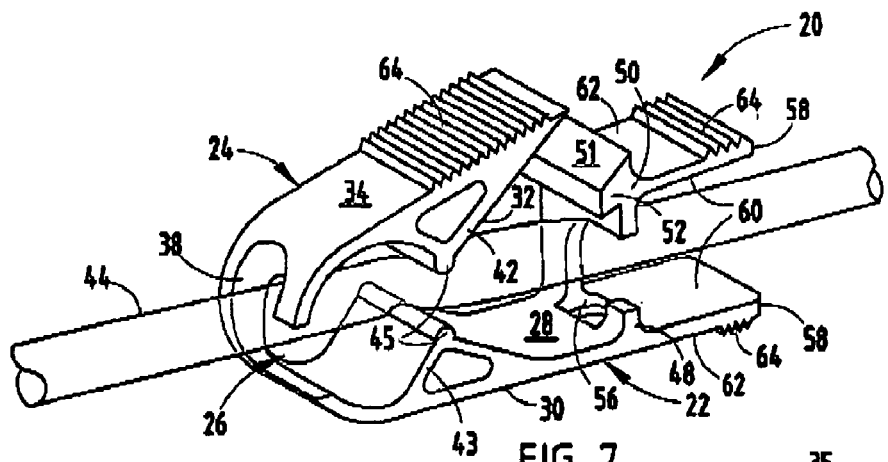
FIG. 7 is a perspective view of a pinch clamp according to an embodiment of the present invention.
Figure 8:
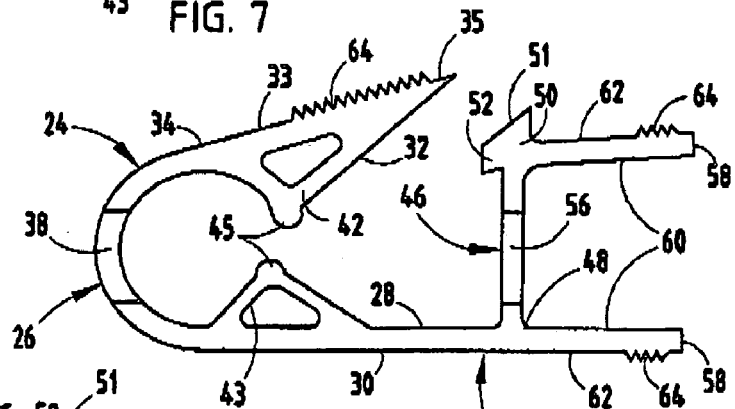
FIG. 8 is a side view of a pinch clamp shown in FIG. 7.

As shown in FIG. 2, a pinch clamp 20 of the present invention generally includes a support leg member 22 and a coupling leg member 24 interconnected with a curved portion 26. The support leg member 22 contains a coupling leg member facing surface 28 and an outer surface 30. The coupling leg member 24 has a support leg member facing surface 32 and an external surface 34. The external surface of the coupling lea member includes an anchoring flange engaging portion 35 and a curved portion engaging section 33 that are in the seine plane as one another. As shown in FIG. 3, the coupling leg member 24 and the support leg member 22 are typically substantially parallel when the coupling leg member 24 is in at least one closed position. As shown in FIG. 2, the curved portion 26 that interconnects the support leg member 22 and the coupling leg member 24 contains a curved portion opening 36. The curved portion opening 36 may be of any size or shape sufficient to receive a hose or other flexible tubing. As shown in FIGS. 7 and 8, the curved portion opening 36 may alternatively be a C-shaped aperture 38.

Typically, the pinch clamps of the present invention are used in conjunction with soft wall tubing having varying outside and inside diameters. The outside diameters of the tubing utilized are typically between about 1/16 inch and about 1½ inches. The flexible tubing may be constructed of latex, rubber, silicone, polypropylene, or any other suitable elastomeric material.

Figure 5:
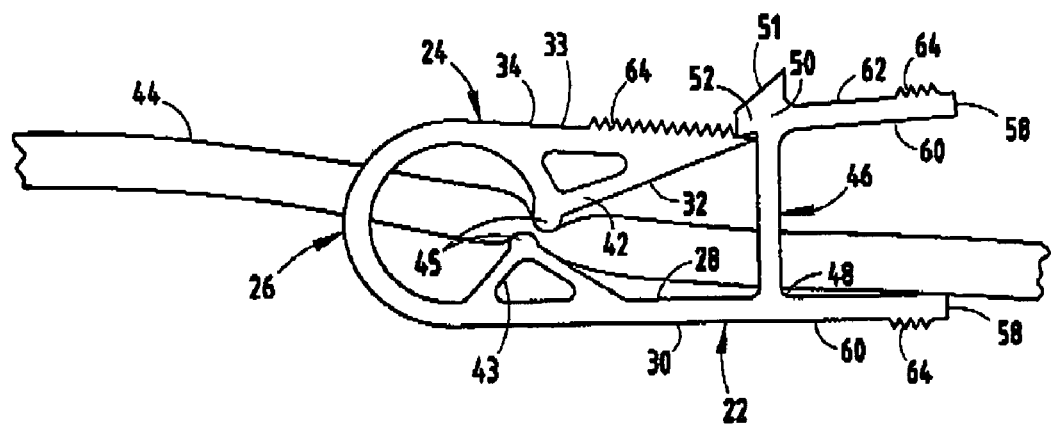
FIG. 5 is a side view of an embodiment of a pinch clamp of the present invention in the closed position.

The pinch clamp 20 further includes a coupling leg pinch portion 42 engaged to the support leg member facing surface 32 of the coupling leg member 24 and a support leg pinch portion 43 engaged to the coupling leg member facing surface 28 of the support leg member. The coupling leg pinch portion 42 and the support leg pinch portion 43 extend inward generally toward one another such that as the coupling leg member is actuated toward the support leg member the pinch portions impede fluid flow through the tubing. When the pinch portions are fully engaged (See FIG. 5), the fluid flow is typically impeded, more typically completely stopped. Also, when the pinch portions are fully engaged (See FIG. 5), the pinch portions are substantially aligned, but slightly offset (See FIG. 5) or aligned with one another (not shown). Typically, for smaller diameter flexible tubing, the slightly offset alignment as shown in FIG. 5 is utilized. When larger diameter tubing is utilized, the pinch portions are typically more closely aligned with one another. Preferably, each pinch portion is generally triangularly shaped with a round point 45 to avoid any potential damage to the tubing from repeated use of the pinch clamp. Typically, the pinch portions are integral with the support leg member 22 and the coupling leg member 24, but could conceivably be separate members engaged with the support leg member 22 and the coupling leg member 24. The pinch portion may also be an indentation or depression in the coupling leg member 24 and/or the support leg member 22. In an alternative embodiment, a single pinch portion extending inward from one of the coupling leg member facing surface 28 of the support leg member 22 or the support leg member facing surface 32 of the coupling leg member 24 may be utilized.

The pinch clamp 20 also includes an upwardly extending anchor portion 46, which may be an upwardly extending portion of the support leg member or may be another member, which is engaged with the coupling leg member facing surface 28 of the support leg member 22. The anchor portion 46 typically includes a base portion 48 and a distal end portion 50. When the anchor portion 46 is not an upwardly extending portion of the support leg member, the base portion 48 engages the coupling leg member facing surface 28 of the support leg member and extending upwardly, typically at about 90 degrees. The anchor portion 46 also includes at least one anchoring flange 52 positioned at least proximate to, but typically at the distal end portion 50 of the anchor portion 46. The anchoring flange 52 faces toward the coupling leg member 24 and engages the coupling leg member 24 when the coupling leg member 24 is in the closed position. The anchoring flange has a top surface 51. The anchor portion 46 further includes an opening 54. Opening 54, like curved portion opening 36, may be of any size or shape significant to receive a hose or other flexible tubing.

Figure 6:
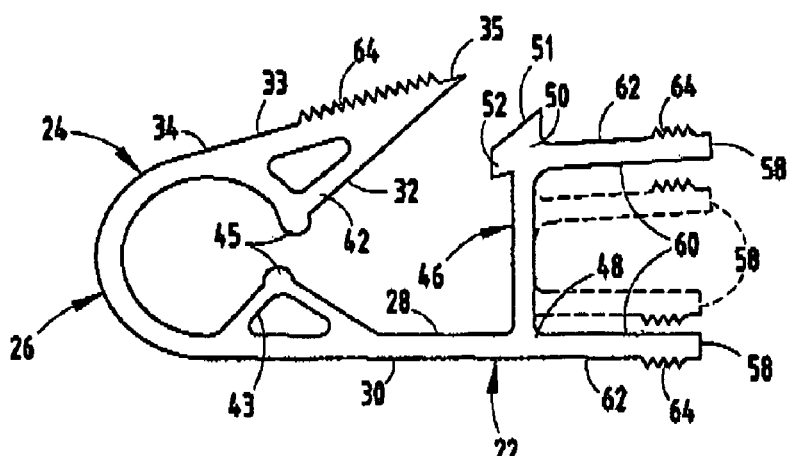
FIG. 6 is a side view of an embodiment of a pinch clamp of the present invention in the open position with alternative positions of the tabular members shown in phantom.

The pinch clamp 20 also typically contains a pair of finger actuated tabular members 58 that extend away from the anchor portion 46 and are typically approximately perpendicular to the anchor portion 46. The finger actuated tabular members 58 typically extend from the distal end portion 50 of the anchor portion 46 and from the base portion 48. The finger actuated tabular members 58 are typically integral with the anchor portion 46 and the support leg member 22. The entire clamp 20 is typically one contiguous structure, but may also be constructed of various individual components as well. The tabular members 58 have an inner tabular surface 60 and an outer tabular surface 62. The tabular members 58 are typically at least substantially aligned with the coupling leg member 24 and the support leg member 22 when the coupling leg member 24 is in at least one closed position; however, the tabular members 58 may be positioned anywhere along the anchor portion 46 (see FIG. 6 in phantom) so long as the tabular members 58, when actuated toward one another, cause the anchor portion 46 to bend, and thereby disengage the anchoring flange 52 and the coupling leg member 24 from one another.

Figure 4:
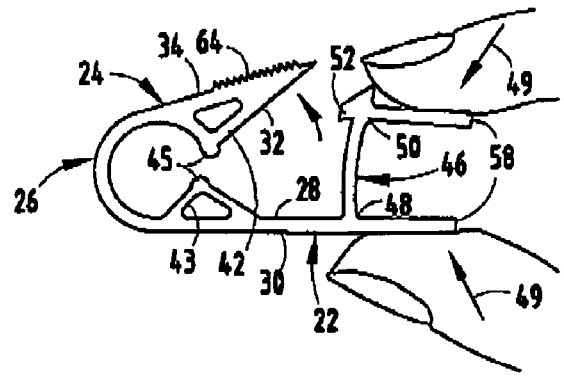
FIG. 4 is a side view of an embodiment of a pinch clamp of the present invention in the process of being opened.
Figure 9:
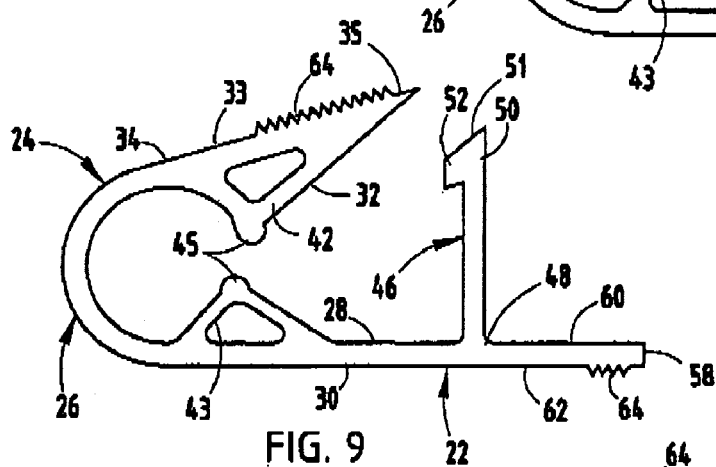
FIG. 9 is a side view of a pinch clamp according to an embodiment of the present invention.

As shown in FIGS. 3–5, in order to unimpede the flow in the tubing 44 and place the coupling leg member 24 in the open position, substantially simultaneous inward forces 49 are applied to the finger actuated tabular members 58. This ergonomic design allows for actuation of the anchor portion 46 and thereby the anchoring flange 52 to release the coupling leg member 24 from any angle and eliminate the hand dexterity required when traditional pinch clamps are utilized. Also, the tabular members 58 may be of any desired length depending on the preference of the user, industry, or both. As shown in FIG. 9, an alternative embodiment includes a single finger actuated tabular member 58 that is typically positioned substantially longitudinal with the support leg member 22. In order to unimpede flow through the tubing in the alternative embodiment with a single finger actuated tabular member 58, sufficient simultaneous inward force should be applied to the finger actuated tabular member 58 and the distal end portion 50. As shown in FIG. 2 and other figures, another alternative embodiment includes a series of ridges 64 that at least partially covers the outer tabular surface(s) 62. Ridges 64 may also be present on the external surface 34 of the coupling member 24. The ridges 64 function to provide a more secure grip when a finger is used to apply force to the surface containing the ridges. Ridges are optional.

In the present invention, the anchor portion 46 and the tabular members 58 are interconnected when the coupling leg member 24 is in the open position. The pinch clamp 20 is preferably made of injected molded plastic material, but may be made from other materials that are sufficiently dexterous and durable such as a metal. Another alternative embodiment includes a pinch clamp 20 made of material that is colored with a dye. Pinch clamps of varying colors may be used to signify different fluids in the hose or tubing or for the purpose of the hose or tubing. This can be of particular importance in the medical field.

Figure 10:
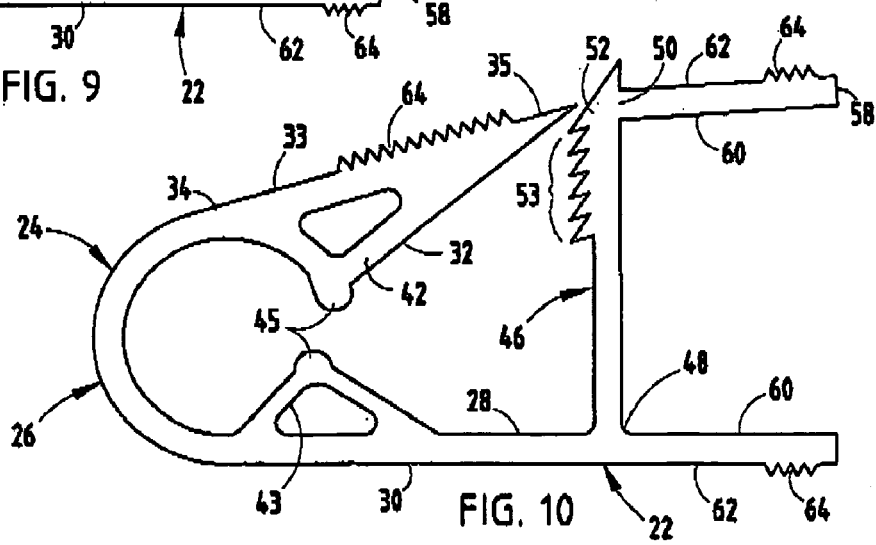
FIG. 10 is a side view of a pinch clamp according to an embodiment of the present invention.

As shown in FIG. 10, an alternative embodiment includes a plurality of anchoring flanges 53 located at the distal end portion 50 of the anchor portion 46. As shown in FIGS. 7 and 8, an alternative embodiment of the anchor portion opening 54 may be a C-shaped aperture 56. The C-shaped aperture 56 of the anchor portion 46 and the C-shaped aperture 38 of the curved portion 26, when utilized together, allows the pinch clamp to be installed or otherwise placed on the tubing without being threaded or otherwise fed onto the tubing. This is advantageous, for example, when the tubing ends have already been connected in a system such as a laboratory apparatus setup. In such an instance, the clamp cannot be threaded or otherwise fed through the apertures unless at least one end of the tubing is disconnected.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A pinch clamp comprising:
   a support leg member comprising a coupling leg member facing surface and an outer surface;
   a coupling leg member comprising a support member facing surface and an external surface, wherein the coupling member is capable of moving between an open position and at least one closed position and vice versa and wherein the coupling and support leg members are substantially parallel when the coupling leg member is in at least one of the closed positions wherein at least the coupling leg member or the support leg member further comprises a pinch portion;
   a curved portion interconnecting the support leg member and the coupling leg member to form a substantially U-shaped clamp body and comprising a curved portion opening;
   an upwardly extending anchor portion comprising a base portion, a distal end portion, at least one anchoring flange, and an anchor portion opening wherein the anchor portion extends upwardly from the support leg member and wherein the at least one anchoring flange faces the curved portion, is positioned at least proximate to the distal end portion of the anchor portion, and is capable of retaining the coupling leg member when the coupling leg member is in the at least one closed position;
   a pair of finger actuated tabular members engaged with the anchor portion wherein the tabular members extend away from the curved portion, and wherein the pair of finger actuated tabular members are adapted to be actuated by applying forces to the tabular members that cause the anchor portion to bend away from the coupling leg member and disengage the coupling leg member from at least one anchoring flange when the coupling leg member is in the closed position; and
   wherein the anchor portion extends upwardly substantially perpendicularly from the coupling leg member facing surface of the support leg member, and wherein the anchor portion, the support leg member, and one of the pair of finger actuated tabular members form a T-shaped juncture.

2. The pinch clamp of claim 1, wherein one of the tabular members engages the distal end portion of the anchor portion and the other tabular member engages the support leg member thereby extending the support leg member beyond the anchoring portion or engages the base portion of the anchor portion; wherein the tabular members are at least substantially parallel with the coupling leg member and the support leg member when the coupling leg member is in at least one closed position; and wherein the anchor portion and the tabular members are interconnected when the coupling leg member is in the open position.

3. The pinch clamp of claim 1, wherein the tabular members further comprise an inner tabular surface and an outer tabular surface and wherein the outer tabular surface of at least one of the tabular members comprises ridges.

4. The pinch clamp of claim 1, wherein the curved portion opening comprises a C-shaped opening, wherein the anchor portion opening comprises a C-shaped aperture, wherein the curved portion opening and the anchor portion opening are substantially aligned and capable of receiving a hose or flexible tubing; and wherein the finger actuated tabular members are adapted to be actuated from any angle by applying substantially simultaneous inward forces; and wherein the external surface of the coupling leg member includes an anchoring flange engaging portion and a curved portion engaging section that are in the same plane as one another.

5. The pinch clamp of claim 1, wherein the coupling leg member includes a pinch portion and the support leg member includes a pinch portion.

6. The pinch clamp of claim 5, wherein the pinch portions are substantially triangular and are at least substantially aligned when the coupling leg member is in the closed position.

7. The pinch clamp of claim 1, wherein the at least one anchoring flange comprises a plurality of adjacent anchoring flanges.

8. The pinch clamp of claim 1, wherein the curved portion opening and the anchor portion opening are at least substantially aligned and capable of receiving flexible tubing having an outside diameter of from 1/16 inch to 1½ inches, and wherein the external surface of the coupling leg member includes an anchoring flange engaging portion and a curved portion engaging section that are in the same plane as one another, and wherein the pair of finger actuated tabular members are substantially parallel to each other.

9. The pinch clamp of claim 1, wherein the upwardly extending anchor portion comprises an upwardly extending portion of the support leg member.

10. The pinch clamp of claim 1, wherein the upwardly extending anchor portion engages the coupling leg member facing surface of the support leg member.

11. The pinch clamp of claim 1, wherein the coupling leg member includes a pinch portion and the support leg member includes a pinch portion and the pinch portions are at least substantially aligned and extend inward from the coupling leg member facing surface of the support leg member and the support leg member facing surface of the coupling leg member.

12. A pinch clamp for pinching and releasing tubing comprising:
   a support leg member comprising a coupling leg member facing surface and an outer surface;

a coupling leg member comprising a support leg member facing surface and an external surface, wherein the coupling leg member is moveable between an open position and at least one closed position and vice versa and wherein the coupling and support leg members are substantially parallel when the coupling leg member is in at least one closed position wherein at least the coupling leg member or the support leg member further comprises a pinch portion;

a curved portion interconnecting the support leg member and the coupling leg member wherein the curved portion comprises an opening;

an upwardly extending anchor portion comprising a base portion, a distal end portion, at least one anchoring flange, and an anchor portion opening wherein the anchor portion extends upwardly from the support leg member and wherein the at least one anchoring flange faces the curved portion, is positioned at least proximate to the distal end portion of the anchor portion, and is capable of retaining the coupling leg member when the coupling leg member is in the at least one closed position; and a first tabular member engaged with the base portion of the anchor portion and extending outwardly away from the curved portion; a second tabular member engaged with the distal end portion of the anchor portion; and wherein the anchor portion and the tabular members are interconnected when the coupling leg member is in the open position and wherein the first and second tabular members are adapted to be actuated by applying substantially simultaneous inward forces to the tabular members that cause the anchor portion to bend away from the coupling leg member and disengage the coupling leg member from the at least one anchoring flange and wherein the external surface of the coupling leg member includes an anchoring flange engaging portion and a curved portion engaging section that are in the same plane as one another, and wherein the upwardly extending anchor portion, the support leg member, and the tabular member engaged with the base portion of the anchor portion form a T-shaped juncture.

13. The pinch clamp of claim 12, wherein the curved portion opening comprises a C-shaped aperture, the anchor portion opening comprises a C-shaped aperture, and wherein the C-shaped apertures are substantially aligned and capable of receiving a hose or flexible tubing through the open side of the C-shaped apertures.

14. The pinch clamp of claim 12, wherein the coupling leg member includes a pinch portion extending toward the support member and the support leg member includes a pinch portion extending toward the coupling member and wherein the external surface of the coupling leg member includes an anchoring flange engaging portion and a curved portion engaging section that are in the same plane as one another.

15. The pinch clamp of claim 12, wherein the at least one anchoring flange comprises a plurality of adjacent anchoring flanges.

16. The pinch clamp of claim 12, wherein the curved portion opening and the anchor portion opening are at least substantially aligned and capable of receiving flexible tubing having an outside diameter of from 1/16 inch to 1½ inches and wherein the second tabular member is at least substantially aligned with the coupling leg member when the coupling leg member is in at least one closed position.

17. A method of using a pinch clamp comprising the steps of:

providing a pinch clamp comprising:

a support leg member comprising a coupling leg member facing surface and an outer surface;

a coupling leg member comprising a support leg member facing surface and an external surface, wherein the coupling leg member is moveable between an open position and at least one closed position and wherein the coupling and support leg members are substantially parallel when the coupling leg member is in at least one closed position wherein at least the coupling leg member or the support leg member further comprises a pinch portion;

a curved portion interconnecting the support leg member and the coupling leg member wherein the curved portion comprises an opening;

an upwardly extending anchor portion comprising a base portion, a distal end portion, at least one anchoring flange, and an anchor portion opening wherein the anchor portion extends upwardly from the support leg member and wherein the at least one anchoring flange faces the curved portion, is positioned at least proximate to the distal end portion of the anchor portion, and is capable of retaining the coupling leg member when the coupling leg member is in the at least one closed position;

a tabular member engaged with the base portion of the anchor portion and extending outwardly away from the curved portion; and a tabular member engaged with the distal end portion of the anchor portion wherein the base portion of the anchor portion and the tabular members are interconnected when the coupling leg member is in the open position; and wherein the upwardly extending anchor portion, the support leg member, and the tabular member engaged with the anchor portion form a T-shaped juncture;

actuating the coupling member to thereby engage at least one anchoring flange; and applying substantially simultaneous inward forces to the tabular members that cause the anchor portion to bend away from the coupling leg member and disengage the coupling leg member from the at least one anchoring flange, and allow the coupling member to return to the open position.

18. The method of using a pinch clamp of claim 17, wherein the external surface of the coupling leg member includes an anchoring flange engaging portion and a curved portion engaging section that are in the same plane as one another and wherein the at least one tabular member of the pinch clamp comprises a pair of tabular members and wherein one of the tabular members engages the distal end portion of the anchor portion, and one of the tabular members engage the base portion of the anchor portion and wherein the step of applying a force that actuates the distal end of the anchoring portion and a force to one of the tabular members comprises applying a force to each tabular member that causes the anchor portion to bend away from the coupling leg member.

* * * * *

UNITED STATES PATENT AND TRADEMARK OFFICE
CERTIFICATE OF CORRECTION

PATENT NO.         : 7,234,677 B2
APPLICATION NO.    : 11/253208
DATED              : June 26, 2007
INVENTOR(S)        : Gerald Bernard Zerfas It is certified that error appears in the above-identified patent and that said Letters Patent is hereby corrected as shown below:

Column 3, line 10;
    "lea" should be --leg--.

Column 3, line 12;
    "seine" should be --same--.

Signed and Sealed this

Thirty-first Day of March, 2009

JOHN DOLL
*Acting Director of the United States Patent and Trademark Office*